(12) United States Patent
Lindal

(10) Patent No.: US 9,895,311 B2
(45) Date of Patent: Feb. 20, 2018

(54) FOAM-FORMING COMPOSITIONS AND METHODS FOR DELIVERING AN ACTIVE TO A BODY CAVITY

(71) Applicant: Ake Richard Lindal, Malmo (SE)

(72) Inventor: Ake Richard Lindal, Malmo (SE)

(73) Assignee: Pharmiva AB, Lund (SE)

( * ) Notice: Subject to any disclaimer, the term of this patent is extended or adjusted under 35 U.S.C. 154(b) by 0 days.

(21) Appl. No.: 14/864,083

(22) Filed: Sep. 24, 2015

(65) Prior Publication Data

US 2016/0089333 A1  Mar. 31, 2016

Related U.S. Application Data

(60) Provisional application No. 62/055,001, filed on Sep. 25, 2014.

(51) Int. Cl.
| | |
|---|---|
| *A61K 9/12* | (2006.01) |
| *A61K 9/10* | (2006.01) |
| *A61K 33/40* | (2006.01) |
| *A61K 47/12* | (2006.01) |
| *A61K 47/14* | (2017.01) |
| *A61K 9/00* | (2006.01) |

(52) U.S. Cl.
CPC .......... *A61K 9/122* (2013.01); *A61K 9/0034* (2013.01); *A61K 9/0043* (2013.01); *A61K 9/0046* (2013.01); *A61K 9/10* (2013.01); *A61K 9/124* (2013.01); *A61K 33/40* (2013.01); *A61K 47/12* (2013.01); *A61K 47/14* (2013.01); *A61K 9/0031* (2013.01)

(58) Field of Classification Search
CPC ........ A61K 33/40; A61K 47/12; A61K 47/14; A61K 9/0031; A61K 9/0034; A61K 9/0043; A61K 9/0046; A61K 9/10; A61K 9/122; A61K 9/124
See application file for complete search history.

(56) References Cited

U.S. PATENT DOCUMENTS

| | | | |
|---|---|---|---|
| 4,684,479 A | 8/1987 | D'Arrigo | |
| 5,554,315 A | 9/1996 | Tonomura | |
| 5,576,016 A * | 11/1996 | Amselem | A61K 9/1075 424/450 |
| 5,693,258 A | 12/1997 | Tnomura | |
| 6,156,294 A | 12/2000 | Mautone | |
| 7,141,237 B2 | 11/2006 | Abram | |
| 7,374,747 B2 | 5/2008 | Abram | |
| 7,709,026 B2 | 5/2010 | Bologna | |
| 7,749,488 B2 | 7/2010 | Abram | |
| 8,193,244 B1 | 6/2012 | Stockel | |
| 8,476,319 B2 | 7/2013 | Scholz | |
| 8,512,723 B2 | 8/2013 | Scholz | |
| 8,586,008 B2 | 11/2013 | Abram | |
| 2007/0292355 A1* | 12/2007 | Tamarkin | A61K 9/12 424/43 |
| 2007/0299043 A1* | 12/2007 | Hunter | A61F 2/0077 514/171 |
| 2008/0299520 A1* | 12/2008 | Ali | A61K 6/0017 433/217.1 |
| 2011/0189637 A1* | 8/2011 | Andersen | A61K 8/33 433/216 |
| 2016/0081968 A1* | 3/2016 | Svensson | A61K 33/38 424/616 |

FOREIGN PATENT DOCUMENTS

| | | | | |
|---|---|---|---|---|
| EP | 0250539 B1 * | 5/1991 | ............. | A01N 59/00 |
| WO | 2006/131784 | 12/2006 | | |
| WO | 2008/075207 | 6/2008 | | |
| WO | WO 2008075207 A2 * | 6/2008 | .......... | A61K 9/0034 |
| WO | 2011/039637 | 4/2011 | | |

OTHER PUBLICATIONS

Attassi F., Servin, A., "Individual and co-operative roles of lactic acid and hydrogen peroxide . . . " FEMS Microbiological letter 394 (2010) 29-38.
Arzhavitina A, Steckel H. "Foams for pharmaceutical and cosmetic application". Int J Pharm. Jul. 15, 2010;394 (1-2):1-17. doi: 10.1016/j.ijpharm.2010.04.028. Epub Apr. 29, 2010.
Written Opinion issued in corresponding international application No. PCT/SE2015/051011, dated Dec. 1, 2016, pp. 1-7.
International Search Report issued in corresponding international application No. PCT/SE2015/051011, dated Dec. 1, 2016, pp. 1-6.
Krog, "Phase behavior and rheological properties of aqueous systems of industrial distilled monoglycerides," Chem. Phys. Lipids 2 (1968) pp. 129-143.

* cited by examiner

*Primary Examiner* — Mark V Stevens
(74) *Attorney, Agent, or Firm* — Jeffrey S. Melcher; Manelli Selter PLLC

(57) ABSTRACT

Provided is a foam-forming formulation and method of treating an infection in a body cavity. The foam-forming formulation contains hydrogen peroxide, monoglyceride crystals, at least one acid and/or buffer which is present in an amount to provide a pH of 3 to 5 within a body cavity, a blowing agent in an amount to blow the foam-forming composition and form a foam, and water. The foam-forming composition is suitable application to body cavity when blown to form the foam and the form degrades at a body temperature to release the hydrogen peroxide to tissues in the body cavity at a pH of 3 to 5. Also provided is a foam-forming composition vehicle for delivering an active agent.

21 Claims, 2 Drawing Sheets

FOAM-FORMING COMPOSITIONS AND METHODS FOR DELIVERING AN ACTIVE TO A BODY CAVITY

This application claims priority to U.S. provisional patent application Ser. No. 62/055,001, filed 25 Sep. 2014, the complete disclosure of which is incorporated herein by reference.

FIELD OF THE INVENTION

The invention relates to foam-forming compositions and methods for delivering an active agent to a body cavity. The invention also relates to a novel foam delivery system and method of delivery.

BACKGROUND OF THE INVENTION

There are several problems associated with the treatment of STI, sexually transmitted infections. The overuse of systemic treatment with active agents, such as antibiotics, has led to development of resistance and the diversity of the diseases, which leads to the need for several treatments with different actives that increase the risk for maltreatment. The difficulty of diagnosing is another issue that can make therapies inefficient. Local treatment has so far been inefficient. The reason for the inefficacy of local treatment is lack of effective local agents. There are numerous germicidal agents available but the concentration to generate an antibacterial effect is about the same as toxic concentrations. One exception is hydrogen peroxide, which is endogenous and nontoxic at low levels. So far attempts to cure vaginal infections with hydrogen peroxide have failed due to effects of peroxide degrading enzymes, catalases. There is also a need for an inexpensive short term treatment since STI is very frequent in development countries with small resources and few medical providers. Development and manufacture of new antibiotics is expensive, while the present invention can be performed locally at a reasonable cost.

Peroxides, and in particular hydrogen peroxide, are described in the literature as being active against anaerobic bacteria involved in vaginal and urinary tube infections represented but not limited to *G. vaginosis, N. gonorrhea*. The activity is rapid, Block, S. Lea & Febiger 1983, p 243, claims 2 log reduction in 7 seconds. However, this is valid only for laboratory conditions. In the clinical situation there are enzymes degrading hydrogen peroxide present in the form of catalases. The catalases are generated partly by plasma cells available in the infected area but also by pathogens such as *G. vaginalis* and *N. gonorrhea*. The catalases are not active at low pH, under pH 4 and have very little activity between pH 4 and 5. The pH in a healthy vagina is about 4.5 or lower and in an infected ditto over pH 5. In men the infection is located in the mucosa of the urethra. The pH here is somewhat higher, about 5 to 8. The present invention solves this problem by providing a pH below 4.5 during the treatment phase allowing eradication of pathogens by hydrogen peroxide. As soon as the pathogens are killed, lactobacteria will be established in the area and pH will be kept low by the present invention.

There have been attempts to develop products including hydrogen peroxide for the treatment of vaginal infections. In clinical use, such as in a body cavity, the activity is rapidly destroyed by enzymes that degrade hydrogen peroxide, e.g. catalases. Since catalases are not active at a pH below 4 and have a much reduced activity in the pH range of 4 to 5 attempts have been made to develop products containing a peroxide source, including hydrogen peroxide, for treatment of vaginal infections by including a pH reducing polyacrylic acid (U.S. Pat. No. 5,741,525). However, such a product is likely to have insufficient storage stability with regard to hydrogen peroxide, is associated with difficulties in effective self-administration and does not to fill the entire cavity following administration leaving untreated areas from which the infection can spread. Furthermore, if unstabilized hydrogen peroxide is exposed to organic matter an auto-oxidation process starts degrading the content of hydrogen peroxide to water and oxygen in seconds or minutes. This will decrease the efficacy and duration of the effect of hydrogen peroxide. The present invention solves these problems by stabilization and auto-oxidation is less likely to occur or occur at a much lower speed.

In U.S. Pat. No. 7,709,026, Bologna et. al., the use of a "hydrogen peroxide" source in combination with a polymer for regulation of the release of peroxides described. As for the previous patent there is no record on stabilization of hydrogen peroxide. No data on the antimicrobial effect is revealed but it should be low since the release of hydrogen peroxide is low, only 26 mM is claimed, and when diluted in the vaginal fluid the concentration of hydrogen peroxide should be further reduced. Since 20 mM or more is required for inhibition of several species even at low pH the product should not be effective. Attassi F., Servin, A., "Individual and co-operative roles of lactic acid and hydrogen peroxide . . . ." FEMS Microbiological letter 394 (2010) 29-38. The present invention solves this problem by releasing instantly, such as 88 mM of hydrogen peroxide at a pH, less than 5, where the catalases are ineffective. This product is also associated with difficulties in effective self-administration and does not to fill the entire cavity following administration leaving untreated areas from which the infection can spread.

Local treatment of diseases in body cavities such as vagina, urethra, ear, anus and the nasal cavity in general require treatment of the entire area in the body cavity. If only a part of the area is treated local infections and inflammations may remain partly untreated. Intra-cavital preparations such as gels, ointments, vagitories/suppositories and tablets have the draw back that only a minor part of the surface is treated. In the case of systemic delivery of active compounds by administration in body cavities the lack of surface coverage means that only a small and from time to time varying area is exposed. This will lead to an unpredictable drug uptake and to a variation in the biological response and medical effect, and risk for resistance development. In contrast, the present novel delivery system is capable of treating the entire surface of a body cavity due to its solid crystalline structure in a composition selected to provide a mechanically stable foam. The body cavities may be natural or artificial body cavities, created by wounds or surgery.

The usefulness of using foams for the treatment of body cavities is well known and described in Arzhavitina A, Steckel H. "Foams for pharmaceutical and cosmetic application". Int J Pharm. 2010 Jul. 15; 394(1-2):1-17. doi: 10.1016/j.ijpharm.2010.04.028. Epub 2010 Apr. 29. Foam containing monoacylglycerides are not common. In U.S. Pat. No. 4,684,479 the use of acylmonoglycerides in foams, formation of microbubbles, is described. There is no information on the melting point and the acylmonoglyceride is not in crystalline form. In U.S. Pat. No. 5,554,315 the use of acylmonoglycerides to improve physical properties of foams based on surfactants, polyoxyalkylene ethers are described. In U.S. Pat. No. 5,693,258 the use of acylmonoglyceride polyoxyethylene derivatives for foams is described. The use of acylmonoglycerides alone or their crystals is not mentioned. In U.S. Pat. No. 7,141,237 and U.S. Pat. No. 7,374,747 the use of higher alcohols, C14 to C22, a small alcohol C1 to C6 water and a surfactant for the generation of a temperature sensitive foam is described. In the presentations of the invention no acylmonoglyceride is mentioned and the formulations contain a surfactant based on an ester of laurinmonoglyceride. In U.S. Pat. No. 7,749,488, a foam consisting of ethanol, water, a surfactant, a pH adjusting compound and a propellant is described in the first claim. The surfactant is defined as a compound from the groups of block-co-polymers, fatty acid and/or fatty alcohol etoxylates, polysorbates and glycerol ester etoxylates. A person skilled in the art may add one or several of the surfactants of these groups to the invented composition for the purpose of improving physical properties, but the invention is based on the use of crystalline lipids and their melting at temperatures below 37° C. which is not taught by this patent. In U.S. Pat. No. 8,193,244 the use of C12 monoacylglycerol in combination with long chain dibasic amino acid alkyl ester salts has been claimed as a synergistic antimicrobial combination, which is not relevant for a foam application. The use of C12 acylmonoglcyeride for the treatment of otitis has been described in U.S. Pat. No. 8,476,319 but there is no teaching of the use of the acylmonoglyceride in crystalline form nor its melting.

In U.S. Pat. No. 8,512,723 the use of C12 acylmonoglyceride is described. However, in this patent the product must contain at least 50% of hydrophobic compound and there is no teaching of the use of the acylmonoglyceride in crystalline form and/or its melting. In U.S. Pat. No. 8,586,008 a foam for topical purposes containing various medical agents is presented. The patent teaches that the melting point of this foam can be regulated with the presence of ethanol. In the invented formulation the melting temperature is regulated by the mixing proportions of acylmonoglycerides. The presence of ethanol increases solubility of the acylmonoglycerides is thereby inhibiting the formation of crystals that is important for the properties of the foam. The patent teaches away from using crystals in the formulation.

Monoglyceride lipid crystals comprising hydrogen peroxide are known for external administration, e.g. on the skin, in the form of creams. The hydrogen peroxide is not formulated to be active in the presence of catalases, the products are not suitable for administration into body cavities, e.g vagina, and the formulation cannot adequately fill a body cavity.

In (Tamarkin) WO2011039637 the main claim in this patent application is "A substantially surfactant free foamable composition comprising: a) about 60% to about 95% by weight of a hydrophobic solvent, or about 1% to about 80%) by weight petrolatum and about 15% to about 94% by weight hydrophobic solvent, wherein if combined the total amount of hydrophobic solvent and petrolatum is at least about 60%>by weight". This patent application does not teach the use of crystalline lipids in a water base to form a foam.

There is a need for improvements in treating infections in body cavities, especially under conditions where classical antibiotics may not be effective and/or where there is a risk for resistance development. There is a need for a product that can be administered immediately upon discovering an infection without any risk of creating antibiotic resistance of the infecting agent and with a high probability of efficient treatment irrespective of the nature the infecting agent, e.g. bacteria, virus, fungi and flagellates.

SUMMARY OF THE INVENTION

The invention solves the problems mentioned earlier by providing a general antiseptic product for local use, hydrogen peroxide (HP), with low irritation profile and with very low or abundant risk for the development of resistance. HP is effective against all microorganisms including bacteria, virus, fungi and flagellates and the treatment can be performed by single administrations. HP is sensitive to the presence of catalases and that is one of the reasons that this active has not come to full use. Catalases are generated by the pathogens involved and by endogenous cells of various origins. In the present invention the catalase is inactivated by the presence of an acid and/or buffer system keeping the pH sufficiently low to inhibit the catalases.

The present invention comprises a suspension or a semi-solid preparation containing crystalline monoglycerides, pressurized with a propellant (blowing agent) to form foam when administered. By administering the product in the form of foam, the entire volume of the cavity can be filled. The foam is constructed to decompose, such as melt, at a body temperature and thereby the entire surface of the cavity will be treated. The product is adapted for local treatment of infections caused by microorganisms sensitive to hydrogen peroxide. The present invention avoids the problem of enzyme degrading HP by using a pH that is unfavorable for the enzyme.

The present invention also relates to a novel foam-forming delivery system comprising solid crystals of lipids that decomposes (melts) at body temperature. The foam is strong and stable at sub decomposition (melting) temperatures thus being able to cover even the narrowest parts of the internal volume of body cavities. Once the volume is covered by the foam, the foam is heated by the body until the foam reaches a decomposition temperature and the crystals melt and the foam breaks due to the body temperature. The melted remains of the decomposed foam, a low viscous fluid, coats the tissues of the body cavity. Such foam is useful for delivery of medically active agents to the interior of body cavities but particularly for systemic delivery via body cavities.

The lipid crystal has a solid form that is sufficient to maintain the foam structure at a temperature below the body temperature (98.6° F. or 37° C.). The foam forming composition comprising lipid crystals and at least one active is stored, and a propellant is used to blow the foam-forming composition and form the foam during application to a cavity. Once the foam is in place within the cavity, the foam is heated by the body. When the foam reaches a decomposition temperature (the decomposition temperature is less than or equal to the body temperature), the lipid crystals melt and the foam breaks down releasing the trapped blowing gas and active agent from the foam to form a layer of active agent on exposed tissue within the cavity.

The invention further relates to a method of administering locally or systemically active agents to tissues within body cavities. As earlier described, there are several problems are associated with intracavital drug administration. A solution to these problems is to deliver the medically active agent in the form of a foam of crystalline lipids that melt at body temperature. The foam has a structure, below the melting temperature, strong enough to allow the foam to be distributed into an entire volume of the cavity while at the same being able to adhere to the entire surface once melted.

The invention further relates to the foam forming composition, disclosed herein, in combination with a delivery device capable of generating a foam of the composition and comprising a foam guiding conduit adapted to provide delivery of the foam into a body cavity.

Objectives of the invention can be obtained by a foam-forming composition adapted for treating a disease in a body cavity comprising:
- a pharmaceutically effective amount of hydrogen peroxide;
- monoglyceride crystals in an amount to form a foam;
- at least one acid and/or buffer which is present in an amount to provide a pH of 3 to 5 within a body cavity;
- a blowing agent in an amount to blow the foam-forming composition and form a foam; and
- water, wherein the foam-forming composition is suitable application to body cavity when blown to form the foam and the form degrades at a body temperature to release the hydrogen peroxide to tissues in the body cavity at a pH of 3 to 5. All are by weight of the total composition unless otherwise stated.

Objectives of the inventions can also be obtained by a foam-forming pharmaceutical composition for delivering an active agent to a body cavity comprising:
- water;
- solid lipid crystals suspended in the water, the solid lipid crystals having a melting point in their crystalline state of less than 37° C. and more than 25° C.; and
- a propellant for blowing the composition and forming a foam, wherein the solid lipid crystals being present in an amount to support a foam when the composition is blown by the propellant, and the composition is adapted for application to the body cavity when blown so that when the foam is heated by the body cavity the foam degrades at the melting point and releases contents of the foam to tissues in the body cavity.

Objectives of the invention can also be obtained by adapting the composition of the foam such that upon melting it contacts the surface of the cavity to deliver e.g. the hydrogen peroxide and the contacting form is resistant to removal by flow of vaginal fluid.

Objectives of the inventions can be obtained by guiding the delivery of the foam formed from the foam-forming compositions to a body cavity with a foam guiding conduit adapted to provide delivery to the entire body cavity.

DETAILED DESCRIPTION OF THE INVENTION

Effects of Hydrogen Peroxide

Figure 1:
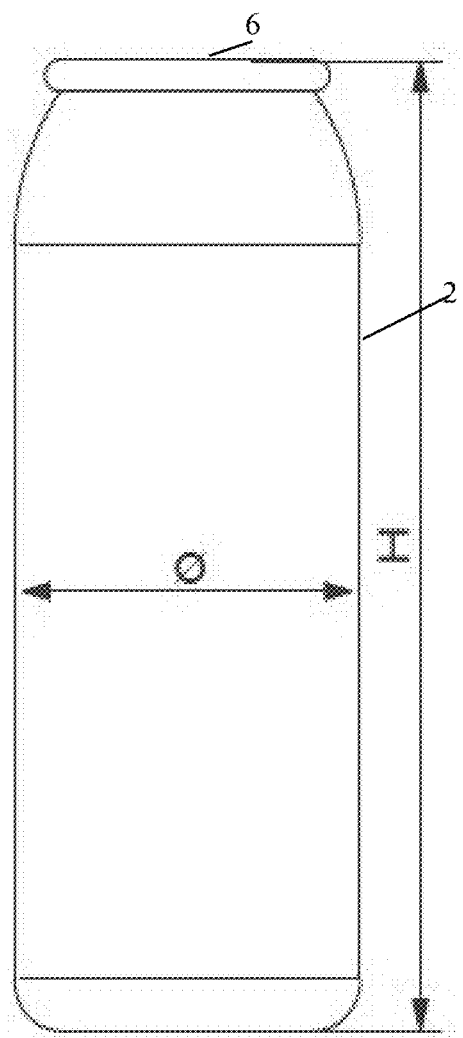
FIG. 1 illustrates an exemplary container.

One problem in the treatment of gonorrhea is the development of resistance towards antibiotics. The antibiotics are specific in their action and operate on the bacteria cell membrane and small alterations in the cell wall synthesis can lead to inactivation of the antibiotic. Antiseptics with less specific action such as peroxides, halogens such as chlorine and iodine, phenols and alcohols, as well as phenolic and nitrogen compounds are less likely to generate resistance due to their general bactericidal effect. However, the lower specificity leads in general to larger risk for toxicity. Of the listed antiseptics most of them are unsuitable for administration into body cavities. One that is suitable is hydrogen peroxide (HP).

It is known that peroxides and in particular HP is an effective antiseptic compound and that most microorganisms are sensitive to HP. We have found that the present invention is capable of eradicating the relevant bacteria when present in a pharmaceutically effective amount. Preferred amounts of HP include from 0.05 to 1%, more preferable 0.05 to 0.5% and most preferable 0.1 to 0.5%. In this application, the content of an ingredient is given in % by weight based on the total weight of the composition.

HP has been administered to humans for over 100 years and one problem that has limited the use of HP has been the auto-oxidation of hydrogen peroxide. This phenomenon leads to a rapid degradation of HP as soon as HP is exposed to reactive matter. The fast reaction leads to boiling, development of oxygen a degradation product of HP, and the HP is consumed within minutes or seconds. With the presence of crystalline acyl monoglycerides, preferably from C12 to C14, the rate of degradation of HP at the site of action can be regulated and optimized for maximum effect. This procedure has been described in the literature for use on skin at higher concentrations of HP. This procedure has however not been demonstrated for use in body cavities, and neither for low amounts of HP, such as 0.5% and below.

HP can be enzymatically degraded, e.g. by catalases and there are at least two sources of catalase in vaginal and urethral infections and that is the naturally occurring catalase from eukaryote cells and the other is the catalase generated by the pathogens, i.e. *N. gonorrhea* and *G. vaginalis*. The catalase is effective at a pH over 5 and in order to avoid this effect the product advantageously contain an alpha hydroxyl acid in an amount sufficient to keep the pH in the body cavity between 3 and 5, preferably between 3.5 and 4.5. Any acid or buffer system suitable for application to a body cavity can be utilized. In the case of the vagina, a preferred acid is lactic acid since lactic acid is already present in the vagina. Other preferred acidifying agents are polymers and oligomers of lactic acid, glycolic acid and acrylic acids or combinations thereof.

The amount of alpha hydroxyl acid in the composition, combinations of monomers and/or oligomers and/or polymers present is preferably 1 to 10%, more preferably 2 to 7%, and most preferably 3 to 6%. In order to operate inside a smaller pH range some of the acid may be replaced by with the salt of the acid or with bases to make a buffer. The final pH should preferably be between 3 and 6, more preferably between 3.5 and 5 and most preferably between 3.5 and 4.5 when exposed to 1 to 10 parts of vaginal fluid.

Lactic Acid

Another important property of the present invention is the ability to regulate pH at the application site. The pH in a healthy vagina is about 4 while the main site of gonorrhea infections for men, the urinary tube, is between 8 and 5 with good opportunities for catalase activity. The present invention contains alpha hydroxyl acids with the purpose of keeping intra-vaginal pH sufficiently low to inhibit the catalases. Preferably, the amount of acid is sufficient to provide a pH below 5 in order to inhibit catalase activity generated by the pathogens or by invading cells, local or from plasma. In order to provide a pH between 3 and 5 the use of at least one buffer based on alpha hydroxyl acids are preferred. A preferred buffer is lactic acid buffer. Preferred pHs are from pH 3 to 5 and more preferably a pH of 3.5 to 4.5. The buffer is preferably present in an amount to be able to keep the pH below 5 when diluted in vaginal or urethral fluids.

Stabilizers for Hydrogen Peroxide

The present invention contains at least one, preferably at least two, and more preferably several stabilizers for HP in order to avoid auto-oxidation. Stabilizers for HP are well-known and any suitable stabilizer can be utilized.

A polycarboxylic acid having a chain length of 2 to 6 carbon atoms, preferably oxalic acid has shown stabilizing effects on HP. The acids can be added to the formulation as salts or as the acid. A most preferred acid of this type is oxalic acid. The acids are preferably added in concentrations between 0.05 and 0.5% and more preferably 0.1 to 0.3%.

Tin, in the form of a salt, either as sodium salt or as a pyrophosphate can be present in an amount of 0.005 to 0.05% or preferably 0.01 to 0.03% corresponding to the amount of tin.

Salicylic acid can be added in an amount of 0.02 to 0.5%, preferably 0.05 to 0.2%. Salicylic acid can also be added as a salt of salicylic acid. Concentrations of Salicylic acid above 0.5% are preferably avoided since above this level pharmacological effects of Salicylic acid could be expected.

Furthermore, the present invention can contain an additional stabilizer in the form of crystalline lipids such as monoglycerides in the amount of 1 to 35%. The monoglycerides are 1-Glycerolmonolaurate, C12, and 1-Glycerolmonomyristate, C14. The amount of and the ratio between C12 and C14 can be varied depending on the required viscosity of the final product. The ratio C12 to C14 can vary from 1 to 3 to 1 to 1 for a cream product and 1 to 3 to 1 to 0 for a lotion/spray form product with lower viscosity. The amount of lipids in a cream can vary between 15 and 35% while lotions and sprays has a preferable lipid content of 1 to 15%. The monoglycerides are in crystalline form in the final formulation. The manufacture of the monoglyceride crystalline dispersion is performed by heating all components, see examples, to 70° C. and cool at a fixed rate, 0.5 to 5° C. per minute, until crystallization starts at 30 to 39° C.

The present invention can be adjusted to a pH with respect to the stability of HP. In this stabilizer combination, the preferred pH during storage was found to be 3.5 to 4.5, which was unexpected in view of the prior art teachings e.g. those of Schumb et al and other authors referred to in the background section. If not buffered the pH in the present invention typically increases after manufacture, e.g. a formulation that immediately after manufacture has a pH of 4.5 will typically increase to pH 5 after a few weeks storage and remain below pH 5.3 for the remaining shelf life period.

Additional stabilizers such as pyrophosphate and sesquestrants, such as but not limited to EDTA and phosphonic acids as well as salicylic acid, are also possible to incorporate into the formulation. Physical stabilisers, against sedimentation of the lipids, such as polar surfactants with HLB over 20 and thickeners such as polyacrylic acid derivatives can also be added to the formulation to improve the foam-forming composition's storage properties. Traditional dermatological humectant agents such as glycerol and propyleneglycol can be added in amounts to enhance humectant properties of the foam composition in contact with mucous tissue and/or skin.

Foam Formulations

The present invention can be in a form that forms a foam when pressurized with a blowing gas when administered, advantageously, a suspension or a low viscosity semisolid and can be pressurized with a blowing gas to form a foam when administered. In the present formulation we have found that a preferable combination of two monoglycerides, C12 monolaurine and C14 monomyristine can create a foam that will decompose when exposed to temperatures above 33° C. This embodiment will describe the preferred use of this foam. However, the formulation can utilize any foam that will decompose when exposed to human body temperatures, including the novel foam delivery system described herein, and convention foams. Thus, any suitable foam forming composition can be used, and the invention is not limited to the preferred examples disclosed herein.

In order to exercise an antimicrobial effect the formulation must be in physical contact with the affected tissue. Local formulations in the form of fluids and semisolids are only in contact with a minor part of the mucosal tissue and are thus not able to exercise its full effect. In the present formulation the foam first fills the entire cavity and secondly the foam decomposes due to the melting of the monoglycerides in the cavity. This way the entire inner surface of the treated body cavity is covered and treated with the formulation when the foam decomposes.

A foam can be generated (blown) by addition of a propellant (blowing agent) suitable for human use, exemplified but not limited to propane and/or butane. Any desired, suitable blowing agent can be used in an amount sufficient to provide the foam during application to the body cavity. An exemplary amount of propellant is from 1 to 20% by weight. The amount of propellant can depend on the desired structure of the foam.

Vaginal or Other Body Cavity Use of the Formulation

The present formulation can be adapted for use in body cavities for the treatment of infections caused by anaerobic bacteria. Examples of suitable body cavities are the vagina, the urinary tube, the anal and the oral cavity. Also infections in the nose and in ears may be treated with this formulation.

Examples of Infections that can be Treated with HP

The active, HP, is active against most microorganisms. Only when the microorgansism can degrade HP, e.g. by catalases or similar enzymes, the antimicrobial capacity is compromised. Since the present formulation avoids this catalase effect, the formulation can be used broadly. Sexually transmitted infections, STI, such as gonorrhea and *candida* as well as bacterial vaginosis and *trichomonas* can be possible to treat successfully with the present invention. Other infections located in the vagina, urethra, anal, oral and nasal region as well as in the ear caused by bacteria sensitive to hydrogen peroxide should be treatable with the present invention.

Body cavity includes not only as natural cavities in contact with the surroundings such as vagina, the mouth and throat, the nasal region, the ear, urethra and rectum but also artificial body cavities such as cavities formed during surgical interventions, dialysis, introduction of prostheses or wounds etc. However, the cavity should be able to access from the outside without causing trauma which excludes cavities in the brain heart and the spine as well as the upper gastrointestinal channel.

Novel Foam Delivery System. The novel HP foam-forming composition disclosed herein is not limited to the novel foam delivery system and can utilize the novel foam delivery system disclosed herein, as well as conventional foam delivery systems.

In one embodiment of the novel foam delivery system, we have invented a formulation that in the presence of a propellant (blowing agent), such as a gas sparingly soluble in water, under pressure to form a liquid, is able to form foams comprising (solid) lipid crystals. Such crystals may comprise single lipids or a mixture of lipids. Suitable lipids are phospholipids, mono and di acylglycerides. N-acetylethanolam ides and esters of lactic acid and fatty acids. Since the lipids are in their crystalline state, the foam will maintain its structure while filling the body cavity. The lipids should be at least partly in their crystalline state, more preferable to 50% and even more preferable to 70% and most preferably to 80% determined by scanning calorimetry.

Crystalline lipids are defined by a continuous repeated structure in three dimensions but the nature of the repetition may not be the same in all directions. The crystals may contain bilayers of water and lipid creating a repeated structure of water and lipid layers in one direction and lipid crystals in two directions. An easy way to detect crystallinity is to study birefringence in microscope. For example, a definition of a lipid lamellar crystal is a solid crystal with three dimensional continuity having the same repeated cells in two dimensions, but a different one in the third dimension, from Small, The lipid handbook, which can be established by wide angle X-ray ref. The crystallinity of monoglycerides in the compositions can be determined by differential scanning calorimetry, DSC. The transfer from solid liquid crystals is exothermic and gives rise to a release of energy. This can be determined by a scanning calorimeter.

There are several advantages associated with the use of (solid) lipid crystals. Since the crystalline state in general is the lowest energetic state very little will happen with the structure during storage. In contrast to emulsions and liquid crystals which are changing over time by crystallization, sedimentation or coalescence, the solid lipid crystalline structures does not change over time in a pharmaceutical perspective. Stable constituents are regarded as a large advantage in the development of pharmaceutical products.

Another important embodiment of the invention is the ability of the foam to decompose (melt) at body temperature or in the body cavity. When lipid crystals melt the gas will be released and the foam will decompose to form a solution that can coat the tissue in the body cavity. The content of the foam, active agents, pH modifying agents, etc. will be released to the tissue and the product can exert its effect. Such foam should preferably melt at a temperature of 25 to 37° C. more preferable at 30 to 37° C. and most preferably at 32 to 37° C.

Yet another embodiment of the invention is the ability to fill the internal volume of a body cavity and to cover a surface once melted to enable medically active agents to be in the formulation to make good contact with the mucosal membrane at the site of administration.

The foam delivery formulations according to the present invention can comprise a solvent or dispersion media, advantageously water. The water can make up the balance of the composition. The solid lipid crystals are present in an amount suitable for forming the foam, for example from 0.5 and 25%. The composition can also include pH and tonicity regulating compounds and pharmaceutically active agents. The formulations can also contain agents for improving foam properties and non-limiting examples are nonionic surfactants of high HLB. Examples of such surfactants are esters of fatty acids and alcohols or saccharides of polar nature.

In a typical but non-limiting procedure the solid lipid crystals are manufactured by heating the lipid(s) in water to 70 to 75° C. to melt the lipids followed by cooling to room temperature to solidify the lamellar crystals. The medically active agent can be added prior to, during or after heating and even after cooling. The cooled dispersion of crystals can then be diluted, if required, and mixed with other agents prior to packing in a pressurized container. Non-limiting examples of such agents are pH modifiers, solvents, viscosity enhancers, chemical and physical stabilizers and preservatives.

In a further embodiment of the invention, the product can be presented in a pressurized container containing a suitable propellant (blowing agent). Non-limiting examples of suitable propellants are propane, n-butane, isobutane and propane. Other suitable propellants include dimethyl ether, methyl ethyl ether, oxygen, nitrogen nitric oxide and carbon dioxide. The amount of propellant is sufficient to form the foam.

Figure 2:
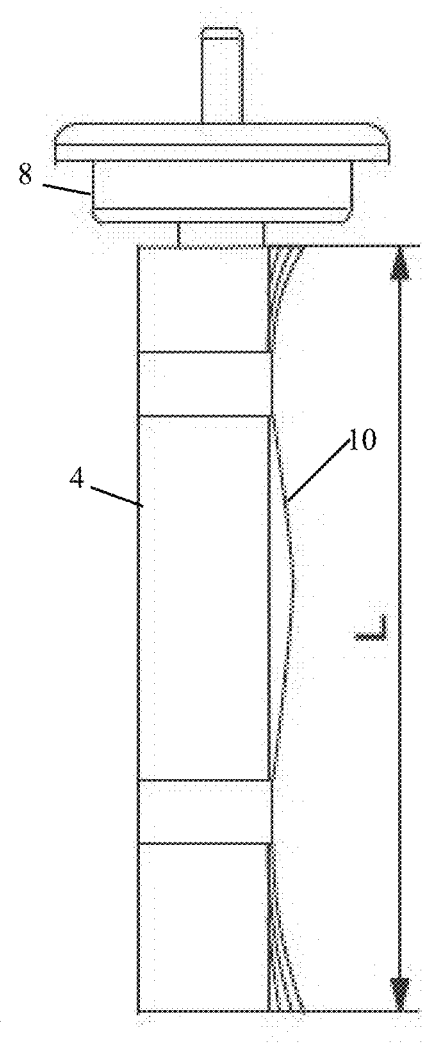
FIG. 2 illustrates an exemplary storage bag.
Figure 3:
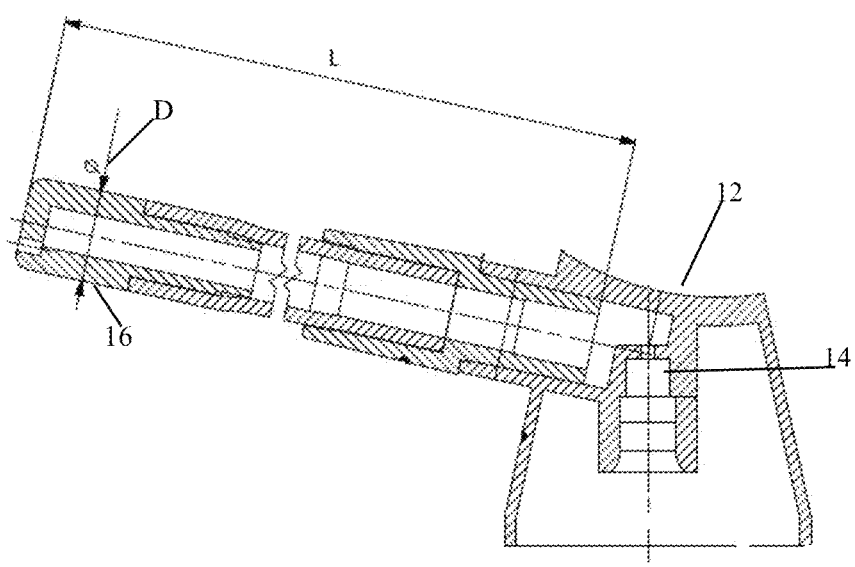
FIG. 3 illustrates an exemplary valve and conduit.

A non-limiting example of a pressurized container according to the invention is shown in FIGS. 1-3, which show a container 2 having an opening 6. The container 2 can be filled with a desired amount of propellant. The bag 4 comprises a laminate bag 10, for example an aluminum and polymer combination, attached to the lid 8 that fits inside the opening 6 of the container 2. After insertion of the lid 8 into the can 2, the bag can be filled with the foam-forming composition and a desired amount of propellant. The lid 8 can be crimped to the container 2 and the spray top 12, including a valve 14 and conduit 16 can be attached. The filling operations can be performed under pressure. The conduit 16 can be sized and adapted to enable administration initially to the parts of the body cavity furthest away from the entrance, e.g. having adequate length L, and thereafter to the outer parts, e.g. while withdrawing the conduit 16 from the body cavity in a controlled and predetermined manner. Suitable sizes for the conduit for vaginal administration are 3 mm to 30 mm, preferably 5 mm to 20 mm in diameter D by 20 mm to 200 mm, preferably 30 mm to 150 mm long L. A non-limiting preferred example of a suitable size for the conduit for vaginal administration is 6.5 mm in diameter D by 121 mm long L, as shown in FIG. 3.

In further embodiments, the foam delivery system can be presented in the form pressurized packaging. This can be of an open interior where all of the propellant is mixed with the product or in the form of a bag on valve container where the product is contained in a small polymeric/sandwich membrane bag inside the container and thus separated from the bulk of the propellant, as shown in FIGS. 1 and 2. Different propellants can be used inside and outside this bag to optimize foam properties and product stability.

In preferred embodiments, the foam delivery system is presented in a pressurized container, packaging, or the like, comprises a foam guiding conduit adapted to provide adequate delivery to all areas of the body cavity to be treated. Based upon the teachings of the present disclosures selection of conduit can be made by one skilled in the art. A preferred example of the pressurized container is shown in non-limiting FIGS. 1-3.

Generally the foam guiding conduit is adapted to result in a coverage of the inner cavity surface greater than that achievable in the absence of the conduit, advantageously complete coverage. In alternative embodiments the coverage can be selected from more than any of: 50%, 60%, 70%, 80% or 90% of the exposed tissue with in the body cavity.

Any desired medically active agent utilized for treating and/or preventing a condition, disease, infection, or other, in a body cavity can be used in the present invention in their pharmaceutically effective amounts. The medically active agents include those described herein, e.g. HP, antibiotics, antifungals, anti-inflammatories, steroids, anticholinergics, and any other desired medically active agent.

In another embodiment the foam can be used for the treatment of local diseases such as infections by bacteria, fungi, virus, parasites or other microorganisms. Non-limiting examples of such infections are bacteria or fungal vaginosis and sexually transmitted infections such as, gonorrhea, syphilis and chlamydia. Other examples are otitis and nasal infections as well as prophylactic treatment against infection or inflammation after surgery.

Other medical indications suitable for treatment by this invented product are local inflammatory processes exemplified but not limited to vulvovaginitis. Suitable compounds are steroids and nonsteroidal anti-inflammatory agents.

Yet other medical indications are preparations for the treatment of ulcers or reduction of scar formation after ulcers generated by surgery or by other causes. Non-limiting examples of suitable compounds are collected from the group of growth factors or compounds having effect on growth factors.

Another medical condition that can be treated with the invented formulation is urinary incontinence. Non-limiting examples of suitable substances are anticholineric compounds such as Oxybutynin, Tolterodine, Darifenacin, Solifenacin, Trospium, Fesoterodine, and bladder relaxing compounds such as Myrbetriq.

The administration of foam to body cavities can be used to treat a systemic disease. Application of a foam to a body cavity can create a large application area and favorable conditions for penetration though or into mucus membranes.

In yet other embodiments of the invention we have found that surface active agents may be useful in the composition. These agents can improve foam properties but also increase the contact between waxy surfaces such as in the ear, and the product.

The invention also relates to methods of treating a condition in a body cavity comprising forming a foam from the foam-forming composition comprising HP, hydrogen peroxide, monoglyceride crystals in an amount to form a foam, at least one acid and/or buffer which is present in an amount to provide a pH of 3 to 5 within a body cavity and water by blowing the foam with a blowing agent in an amount to blow the foam-forming composition and form the foam. The methods include applying the foam to a body cavity to coat tissues in the body cavity with the foam composition with the blowing agent and allowing the body to heat the foam to a decomposition temperature of the foam, wherein the foam degrades and releases the HP to the tissues in the body cavity at a pH of 3 to 5. The foam can be guided by a foam guiding conduit.

The invention also relates to a method of delivering an active agent to tissues in a body cavity comprising forming a foam from a foam-forming pharmaceutical composition for delivering an active to a body cavity comprising water, an active agent, and solid lipid crystals suspended in the water, the solid lipid crystals having a melting point in their crystalline state of less than 37° C. and more than 25° C. by blowing the foam-forming composition with a blowing agent. Applying the foam to a body cavity to coat tissues in the body cavity with the foam-forming composition with the blowing agent. Allowing the body to heat the foam to a decomposition temperature of the foam, wherein the foam degrades and releases the active agent to the tissues in the body cavity. The foam can be guided by a foam guiding conduit.

EXAMPLES

Stabilized Formulations Variations of HP/Monoglycerides/Lactic Acid

Example 1

The formulations in table 1 were manufactured and tested for content of HP by a permanganate titration method, USP, assay for HP. The manufacture was performed according to the following procedure. EDTA, sodium stannate, sodium pyrophosphate, and sodium oxalate were dissolved in water. If applicable, thickening agents are included at this point. Lactic acid and sodium hydroxide were added and pH adjusted. The monoglycerides were added and the mixture was heated to 70 to 75 C and kept there for 15 minutes while stirring. After 15 minutes slow cooling, less than 5 C per minute, was applied to about 35 when crystallization occurred followed by an increase in temperature. After the crystallization was completed hydrogen peroxide was added. The products were packed in glass ampoules and stored at 30, 50 and 70° C. Samples were withdrawn at 2, 4 and 7 days for the 70° C. stored products and at 7, 14 and 30 days for the samples stored at 50° C. and at 30 and 90 days for the products stored at 30° C. Analysis of the content of HP was made by a titration method including dissolution of the compositions in acetic acid and titration to color shift by potassium permanganate.

TABLE 1

Formulations for stability testing (% w/w).

| | A | B | C | D | E | F |
|---|---|---|---|---|---|---|
| EDTA | 0.05 | 0.05 | 0.05 | 0.05 | 0.05 | 0.05 |
| Sodium pyrophosphate | 0.025 | 0.025 | 0.025 | 0.025 | 0.025 | 0.025 |
| Sodium stannate | 0.04 | 0.04 | 0.04. | 0.04 | 0.04 | 0.04 |
| Sodium oxalate | 0.14 | 0.14 | 0.14 | 0.14 | 0.14 | 0.14 |
| Lactic acid (90%) | 5.00 | 5.00 | 5.00 | 5.00 | 5.00 | 5.00 |
| Glycerol monolaurate | 0.625 | 0.625 | 0.625 | 2.5 | 0.625 | 0.625 |
| Glycerol monomyristate | 1.875 | 1.875 | 1.875 | 7.5 | 1.875 | 1.875 |
| H2O2 | 0.3 | 0.3 | 0.3 | 0.3 | 0.1 | 0.5 |
| 10M NaOH | 3.00 | 3.00 | 4.00 | 3.00 | 3.00 | 3.00 |
| Xanthan gum | | 0.5 | | | | |
| HPLC water | To 100 | To 100 | To 100 | To 100 | To 100 | To 100 |
| pH | 3.5 | 3.5 | 4.5 | 3.5 | 3.5 | 3.5 |
| Stability* | | | | | | |
| Initial | 3.20 | 3.20 | 3.19 | 3.31 | 1.24 | 5.29 |
| 70 C. 4 days | 2.42 | 2.37 | 2.55 | 2.32 | 0.85 | 3.93 |
| 50 C. 14 days | 2.29 | 1.89 | 2.41 | 2.25 | 0.70 | 3.97 |
| 30 C. 30 days | 2.74 | 2.65 | 2.74 | 2.77 | 0.87 | 4.56 |

*Remaining amount of hydrogen peroxide (mg/g)

Example 2, Foam Forming

We have studied the effect of the amount of lipids on the ability to form a foam and the stability of HP. The formulations were manufactured according to example 1 and aerosols were produced by, under pressure, adding 8% of a mixture 50/50 of pharmaceutical grade propane and butane into an aerosol container having an inner container of a polymer protecting the product against the metal material in the container.

TABLE 2

Foaming versus amount of monoglycerides(%)

| Ingredient | 1 | 2 | 3 |
|---|---|---|---|
| Hydrogen peroxide | 0.3 | 0.3 | 0.3 |
| 1-glyceryl-monolaurate | 2.5 | 5 | 1.25 |
| 1-glyceryl-monomyristate | 7.5 | 15 | 3.75 |

TABLE 2-continued

Foaming versus amount of monoglycerides(%)

| Ingredient | 1 | 2 | 3 |
|---|---|---|---|
| Myrj 59 | 0.1 | 0.1 | 0.1 |
| Sodium stannate | 0.04 | 0.04 | 0.04 |
| Sodium pyrophosphate | 0.025 | 0.025 | 0.025 |
| Sulphuric acid | 0.038 | 0.038 | 0.038 |
| EDTA | 0.05 | 0.05 | 0.05 |
| Oxalic acid | 0.14 | 0.14 | 0.14 |
| Lactic acid | 5.0 | 5.0 | 5.0 |
| Sodium hydroxide | 0 | 0 | 0 |
| Purified water to | 100 | 100 | 100 |
| pH | 4 | 4 | 4 |
| Butane gas | 8 | 8 | 8 |

All three batches produced a white solid foam when released from the can when observed by the naked eye.

Example 3. The Effect of Using Stabilizers in Aerosols

Three batches were manufactured according to Example 1 and tested for stability of HP using the method of Example 1. Aerosols were produced by first manufacturing the formulations 1, 2 and 3 according to Table 2 and then under pressure adding 8% of a mixture 50/50 of pharmaceutical grade propane and butane into an aerosol pressure container having an inner container of a polymer protecting the product against the metal material in the container. Stability was tested both for the pressurized containers and for product stored in polyethylene containers at atmospheric pressure.

TABLE 3

Compositions in % (w/w).

| Ingredients | ISM14123 | ISM14124 | ISM14125 |
|---|---|---|---|
| Monolaurine | 2.5 | 2.5 | 2.5 |
| Monomyristine | 7.5 | 7.5 | 7.5 |
| EDTA | — | 0.05 | 0.05 |
| Sodium pyrophosphate | — | 0.025 | 0.025 |
| Sodium stannate | — | 0.04 | 0.04 |
| Sodium oxalate | — | 0.14 | 0.14 |
| Hydrogen peroxide | 0.3 | 0.3 | 0.3 |
| Lactic acid | 5 | 5 | 5 |
| 10M NaOH | To pH 3.5 | To pH 3.5 | To pH 3.5 |
| Tween 80 | — | — | 3 |
| Span 40 | — | — | 1 |
| Water to | 100 | 100 | 100 |
| Propane/butane 50/50 | 8 | 8 | 8 |
| Remaining after 6 months at 30 C. (%) with gas. | 0.082 | 0.174 | 0.183 |
| Remaining after 6 months at 25 C. (%) with gas. | 0.136 | 0.204 | 0.204 |
| Remaining after 6 months at 30 C. (%) without gas. | 0.050 | 0.194 | 0.191 |
| Remaining after 6 months at 25 C. (%) without gas. | 0.093 | 0.221 | 0.222 |

This example concludes that introduction of the salts increased stability of HP and that the introduction of surfactants did not affect stability.

Example 4 Stability of HP at 2 to 8 C in the Invented Formulation

TABLE 4

Stability of HP in the present composition in a pressurized container.

| Composition (%) | D |
|---|---|
| EDTA | 0.05 |
| Sodium pyrophosphate | 0.025 |
| Sodium stannate | 0.04 |
| Sodium oxalate | 0.14 |
| Lactic acid (90%) | 5.00 |
| Glycerol monolaurate | 2.5 |
| Glycerol monomyristate | 7.5 |
| H2O2 | 0.3 |
| 10M NaOH | 3.00 |
| HPLC water | To 100 |
| Propellant, butane | 8 |
| pH | 4.2 |
| Stability* | |
| Initial | 3.33 |
| 25° C. 3 months | 2.8 |
| 2-8° C. 3 monhs | 3.32 |

*Remaining amount of HP (mg/g)

Manufacture was performed according to Example 1 and the composition was packed in aluminum containers equipped with an inner bag made of aluminum/polymer laminate. The propellant (blowing agent) amount noted in table 4 refers to the amount of propellant in contact with the composition. The product demonstrated a slight degradation at 25° C. but is stable at 2 to 8° C.

Example 5. Effect on N. gonorrhea

A product according to Table 5 was tested for effect against Neisseria gonorrhea in a medium containing catalase producing cells from sheep blood and from the pathogen itself. The product was manufactured according to Example 1.

TABLE 5

| Ingredients | % (w/w) |
|---|---|
| EDTA | 0.050 |
| Sodium pyrophosphate | 0.025 |
| Sodium stannate | 0.040 |
| Sodium oxalate | 0.14 |
| Lactic acid | 5.00 |
| Sodium hydroxide | 1.00 |
| Glycerol monolaurate | 2.50 |
| Glycerol monomyristate | 7.50 |
| Hydrogen peroxide 30 wt % | 1.00 (0.3% $H_2O_2$) |
| HPLC water | 82.745 |

The product is diluted with Muller Hinton agar, with sheep blood and without, in the following proportions, 1:1, 1:10 and 1:15, and inoculated on petri discs with a freshly made suspension of N. gonorrhea.

Results.

In all dilutions, 1:1, 1:10 and 1:15 N. gonorrhea were eradicated. A placebo was included and on this disc strong growth was seem. The formulation was also diluted 1:1000 and on these discs strong growth was detected.

This example demonstrates a strong antimicrobial effect in spite of the presence of catalases.

Example 6 Effect on *Gardnerella vaginalis*

In this example we have included formulations containing the active, monoglycerides and lactic acid. The formulations were manufactured according to Example 1. We have tested the minimum inhibitory concentration by adding decreasing amounts of the active to a broth containing the pathogen.

TABLE 6

Formulations (%).

| Ingredient | ISM13183 | ISM13184 | ISM13185 | ISM13186 | ISM13187 |
|---|---|---|---|---|---|
| Lactic acid | 5 | 5 | 5 | 5 | 5 |
| Monolaurine | 5 | 0 | 0 | 5 | 5 |
| Monomyristine | 15 | 0 | 0 | 15 | 15 |
| Hydrogen peroxide | 0.3 | 0.3 | 0 | 0 | 0.1 |
| Water, purified | 74.7 | 94.7 | 95 | 75 | 74.9 |

TABLE 7 results of inhibition tests.

| Ingredient | ISM13183 | ISM13184 | ISM13185 | ISM13186 | ISM13187 |
|---|---|---|---|---|---|
| Lactic acid | 5 | 5 | 5 | 5 | 5 |
| Monolaurine | 5 | 0 | 0 | 5 | 5 |
| Monomyristine | 15 | 0 | 0 | 15 | 15 |
| Hydrogen peroxide | 0.3 | 0.3 | 0 | 0 | 0.1 |
| Water | 74.7 | 94.7 | 95 | 75 | 74.9 |
| Zone inhibition Conc(%)* | | | | | |
| 50 | | I | I | I | I |
| 40 | | I | | | |
| 30 | | I | | | |
| 20 | | I | | | |
| 15 | | N | | | |
| 10 | | N | | I | I |
| 7.5 | | | | | |
| 5 | | I | | | |
| 3 | | I | | | |
| 2.5 | I | I | | | |
| 2 | I | N | | | |
| 1 | I | N | N | I | I |

*% of product in the mixture of broth and product.
I = inhibition
N = No inhibition The results indicate a strong effect of hydrogen peroxide when the crystalline monoglycerides are present while hydrogen peroxide in combination with lactic acid is less effective and lactic acid on its own is ineffective after about 5 times dilution.

Example 7, Foam Properties

Melting point of foam was determined.
The formulations according to table 8 were manufactured according to Example 1.

TABLE 8

Formulations for melting point test.

| Ingredients | G | H | I |
|---|---|---|---|
| 1-Glycerylmonomyristate | 6 | 9 | |
| 1-Glycerylmonolaurate | 3 | | 9 |
| Lactic acid | 3.6 | 3.6 | 3.6 |
| Hydrogen peroxide | 0.27 | 0.27 | 0.27 |
| Sodium hydroxide | 0.9 | 0.9 | 0.9 |
| Water | 77.23 | 77.23 | 77.23 |
| Melting point (° C.) | 34 | 41 | 39 |

Method and results: The melting of the formulations was tested by differential scanning calorimetry, DSC. A DSC 7 was used and about 5 mg of each formulation was weighed and put in aluminum containers. The melting peak of the preparations were determined by first cooling to about 0 C and then heating to 50 C at a rate of 5 C per minute.

The results show that a combination of the two monoglycerides makes the composition melt when heated to body temperature and provide even application of the active to the affected tissue in the body cavity.

Example 8 Manufacture of the Formulation and Content of Lipids

TABLE 10

Compositions (g)

| Invented composition | 1A | 1B |
|---|---|---|
| EDTA | 0.050 | 0.050 |
| Sodium pyrophosphate | 0.025 | 0.025 |
| Sodium stannate | 0.040 | 0.040 |
| Sodium oxalate | 0.14 | 0.14 |
| Lactic acid | 3.00 | 3.00 |
| Glycerol monolaurate | 0.2 | 7 |
| Glycerol monomyristate | 0.4 | 21 |
| NaOH | 0.70 | 0.70 |
| Hydrogen peroxide 30 w % | 1.00 | 1.00 |
| Propellant | 10 | 10 |
| HPLC water | 94.445 | 67.045 |

The formulations were manufactured by heating of water to 75 C, dissolving the salts and lactic acid in said water, the first 5 items on the ingredient list, and addition of the monoglycerides. After 15 minutes at 75 C the monoglycerides are melted and the mixture is cooled slowly to about 30 C to obtain crystallization and the cooling is stopped. After crystallization, visible as an increase in reflection of light from the composition, cooling to ambient temperature, <25 C, was undertaken. The pH was adjusted with sodium hydroxide and hydrogen peroxide was added. The manufactured compositions were packed in bulk containers.

Products, suspensions of crystalline lipids in water manufactured according to Example 1 and with compositions according to Table 10 were packed under pressure in two types of pressure containers, bag on valve which is a dual compartment packaging and a single compartment packaging device. Packing in bag on valve, BOV, pressure packs were made by using a manual filling equipment. At first the composition was filled, then gas was filled outside the bag on valve and finally the gas inside the bag on valve (in contact with the composition). The gas used in contact with the composition was butane alone while the gas outside the bag was a mixture of butane and propane.

TABLE 11

Composition, one compartment pressure container.

| | Type | Amount |
|---|---|---|
| Product | 1A | 10 g |
| Gas (propellant) | Butane | 1 g |

TABLE 12

Composition, bag on valve.

| | Type | Amount |
|---|---|---|
| Product | 1A | 10 g |
| Gas (propellant) in bag | Butane | 1 g |
| Gas (propellant) in pressure container | Butane/Propane | 1 g |

From aerosol packing point of view both types of packages are possible to use since a solid white foam that melted at about 35° C. was generated.

Example 9. Foam Stability

Two foam products, one commercial and one according to the invention, are manufactured and pressure packed, and the foam stability is tested by a modification of an EP method for testing foam stability.

TABLE 13

Composition of invented foam (g).

Present Invention

| | |
|---|---|
| EDTA | 0.050 |
| Sodium pyrophosphate | 0.025 |
| Sodium stannate | 0.040 |
| Sodium oxalate | 0.14 |
| Lactic acid | 3.00 |
| Glycerol monolaurate | 2.50 |
| Glycerol monomyristate | 7.50 |
| NaOH | 0.70 |
| Hydrogen peroxide 30 w % | 1.00 |
| HPLC water | 85.045 |
| Butane inside bag | 4 |
| Butane/propane outside bag (in pressure container) | 10 |

TABLE 14

Commercial foam.

Composition from U.S. Pat. No. 7,749,448

| | |
|---|---|
| Dehydrated Alcohol (Ethanol), USP | 58.98 |
| Cetyl Alcohol, NP | 1.16 |
| Stearyl Alcohol, NP | 0.53 |
| Polysorbate 60, NP | 0.42 |
| Propylene Glycol, USP | 2.11 |
| Purified Water, USP | 36.69 |
| Potassium Hydroxide, USP, 10% W/W soln. | 0.11 |
| Butane inside bag | 4 |
| Butane + propane outside bag (in pressure container) | 10 |

Foam Stability and Adhesion Test.

A glass tube, volume 60 ml, with a diameter of 26 mm was heated to 37° C. in a waterbath. The glass tube was removed and was turned upside down. The foams were administered into the tube through a foam guiding conduit until it was full by a controlled procedure comprising initially filling the cavity volume furthest away from the opening and then withdrawing the conduit to optimize foam delivery. The tube was then returned to the water bath. The spreadability, melting and adhesion to the tube surface was studied.

Results:

The invented foam filled the volume of glass tube completely and rapidly. After about 30 seconds in the water bath it started to melt and adhered to the surface. The entire internal surface of the glass tube was covered with the melted foam as observed by the naked eye. The prior art foam broke at contact with the surface and did not fill the volume and only a part of the inner surface of the tube was covered with the prior art foam.

Example 10, Formulations Intended for Local Treatment of Vaginal Infections

TABLE 15

Example of a composition of a 3 mg/g hydrogen peroxide vaginal foam.

| Ingredients | Quantity % (w/w) |
|---|---|
| Hydrogen peroxide | 0.3 |
| EDTA | 0.05 |
| Sodium pyrophosphate | 0.025 |
| Sodium stannate | 0.04 |
| Sodium oxalate | 0.14 |
| Glycerol monolaurate | 2.5 |
| Glycerol monomyristate | 7.5 |
| Lactic acid (90%) | 3.0 |
| Sodium hydroxide | 3.0 |
| Water demineralized | 83.745 |
| Total | 100.00 |
| Butane | 10 |

A formulation useful for the treatment of vaginal infections is presented in table 8. The formulation is useful for the treatment of infections caused by microorganisms that are sensitive to hydrogen peroxide. Non limiting examples of such bacteria are associated with bacterial vaginosis, fungal infections, gonorrhea, syphilis and chlamydia. It is also locally effective against virus.

Example 11, Formulations Intended for Local Treatment of Infections if the Ear or in the Nasal Cavity

TABLE 16

Example of a composition of a 5 mg/g hydrogen peroxide vaginal foam.

| Ingredients | Quantity % (w/w) |
|---|---|
| Hydrogen peroxide | 0.5 |
| EDTA | 0.05 |
| Sodium pyrophosphate | 0.025 |
| Sodium stannate | 0.04 |
| Sodium oxalate | 0.14 |
| Glycerol monolaurate | 2.5 |
| Glycerol monomyristate | 7.5 |
| Lactic acid (90%) | 3.0 |
| Sodium hydroxide | 3.0 |
| Surfactant, Tween 20. | 1.0 |
| Water demineralized | 82.24 |
| Total | 100.00 |
| Butane | 10 |

Example 11 formulations intended for local treatment of inflammatory processes in body cavities.

Suitable compounds comprise nonsteroidal anti-inflammatory drug, and/or corticosteroids. In Table 17 an example of a foam steroid formulation is described. The steroid is dissolved in the propellant and is homogenously distributed in the product.

TABLE 17

Example of a composition of a 5 mg/g Mometasone vaginal foam.

| Ingredients | Quantity % (w/w) |
|---|---|
| Mometasone | 0.5 |
| Glycerol monolaurate | 2.5 |
| Glycerol monomyristate | 7.5 |
| Lactic acid (90%) | 3.0 |
| Sodium hydroxide | 3.0 |
| Water demineralized | 83.24 |
| Total | 100.00 |
| Butane | 10 |

Example 12, Formulations Intended for Administration to the Vagina for Systemic Treatment of Urinary Incontinence Examples of suitable substances are anticholineric compounds such as Oxybutynin, Tolterodine, Darifenacin, Solifenacin, Trospium, Fesoterodine, and bladder relaxing compounds such as Myrbetriq.

Composition.

TABLE 18

Example of a composition of a 1 mg/g Tolterodine vaginal foam.

| Ingredients | Quantity % (w/w) |
|---|---|
| Tolterodine tartrate | 0.1 |
| Glycerol monolaurate | 2.5 |
| Glycerol monomyristate | 7.5 |
| Lactic acid (90%) | 3.0 |
| Sodium hydroxide | 3.0 |
| Water demineralized | 83.24 |
| Total | 100.00 |
| Butane | 10 |

Example 13, Adhesion Test

To investigate the ability of the present foam to adhere to surfaces the following experiment was performed. About 0.4 g of the product according to an Example 9, Tale 13, was filled into a polypropylene test tube of 4 ml. The tube was heated in a waterbath to 37 C and the foam melted and poured out of the test tube by turning it upside down. The test tube was then washed repeatedly with 0.5 ml of artificial vaginal fluid having a pH of 7.2. The wash fluid was tested for presence of hydrogen peroxide using a peroxide test (MQvant) that is able to detect >25 mg/l and quantatively between 25 and 0.5 mg/l. The composition of the artificial vaginal fluid is shown in table MM and is taken from a paper by Maria S. J. Tomas and Maria E. Nader-Macias "Effect of medium simulating . . . " in Communication current research and educational topics and trends in applied microbiology, pp. 732-739, 2007.

TABLE 18

Composition of vaginal fluid.

| Ingredient | Concentration g/L |
|---|---|
| Glucose | 10.0 |
| Glucogen | 10.0 |
| Lactic acid | 2.0 |
| Acetic acid | 1.0 |

TABLE 18-continued

Composition of vaginal fluid.

| Ingredient | Concentration g/L |
|---|---|
| Albumin | 2.0 |
| Urea | 0.5 |
| Sodium chloride | 3.5 |
| Potassium chloride | 1.5 |
| Tween 80 | 1.064 |
| Cystein HCl | 0.5 |
| Mucin | 0.25 |
| pH | |

The artificial vaginal fluid was adjusted with potassium dihydrogen phosphate, dibasic potassium phosphate and potassium hydroxide to pH 7.2. The results indicate that hydrogen peroxide remains on the surface although diluted with wash fluid suggesting adhesion of the product to the test tube.

TABLE 19

Remaining hydrogen peroxide after repeated washings

| Dilution with artificial vaginal fluid | Content of $H_2O_2$ by MQvant test |
|---|---|
| 0.5 ml | >25 mg/l |
| 0.5 ml | >25 mg/l |
| 0.5 ml | 10-25 mg/l |
| 0.5 ml | 5 mg/l |
| 0.5 ml | 2 mg/l |
| 0.5 ml | 2 mg/l |
| 0.5 ml | 2 mg/l |
| 0.5 ml | 2 mg/l |
| 0.5 ml | 2 mg/l |
| 0.5 ml | 2 mg/l |

The experimental results described herein demonstrate that surprisingly the monoglycerides stabilize the hydrogen peroxide in the pressurized foam-forming formulation, whereas other foam-forming formulations do not stabilize the hydrogen peroxide. Without being bound by any theory, it is believed that the monoglycerides inhibit auto-oxidation of hydrogen peroxide in the foam-forming formulation.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A foam-forming pharmaceutical composition for delivering hydrogen peroxide to a body cavity comprising: water; a pharmaceutically effective amount of hydrogen peroxide;
solid lipid crystals suspended in the water and having a continuous repeated structure in three dimensions in which the repeated structure is bilayers of water and the solid lipid crystals in one direction, the solid lipid crystals having a melting point in their crystalline state of less than 37° C. and more than 25° C.; and
a propellant for blowing the composition and forming a foam, wherein the solid lipid crystals being present in an amount to support a foam when the composition is blown by the propellant, and the composition is adapted for application to the body cavity when blown so that when the foam is heated by the body cavity the foam degrades at the melting point and releases the hydrogen peroxide to tissues in the body cavity, wherein the propellant consists essentially of at least one blowing agent selected from the group of nitrogen, oxygen, or carbon dioxide.

2. The foam-forming composition according to claim 1, wherein the lipid crystals are selected from the group consisting of phospholipids, mono or di acylglycerides, lipid esters of lactic acid, and n-acetylethanolam ides.

3. The foam-forming composition according to claim 1, wherein the lipids being present in an amount of at least 0.5% and at the most 28% by weight based on the weight of composition.

4. The foam-forming composition according to claim 1, the composition is packed in single or dual compartment containers.

5. The foam-forming composition according to claim 1, wherein the lipid comprises monoacylglycerides having a carbon chain length of 10 to 16 carbons and where the relation between the monoacylglycerides are 1:20 to 20:1.

6. The foam-forming composition according to claim 1, wherein the hydrogen peroxide is present for the treatment of infections in body cavities.

7. A foam-forming composition adapted for treating a disease in a body cavity comprising: water;
a pharmaceutically effective amount of hydrogen peroxide;
monoglyceride crystals in an amount to form a foam, the monoglyceride crystals being suspended in the water and having a continuous repeated structure in three dimensions in which the repeated structure is bilayers of water and the monoglyceride crystals in one direction;
at least one acid and/or buffer which is present in an amount to provide a pH of 3 to 5 within a body cavity; and
a blowing agent in an amount to blow the foam-forming composition and form a foam, wherein the foam-forming composition is suitable application to body cavity when blown to form the foam and the form degrades at a body temperature to release the hydrogen peroxide to tissues in the body cavity at a pH of 3 to 5, and wherein the blowing agent consists essentially of at least one blowing agent selected from nitrogen, oxygen, or carbon dioxide.

8. The foam-forming composition according to claim 7, wherein the monoglyceride crystals comprise at least two monoglycerides having an average chain length of 12 and 14.

9. The foam-forming composition according to claim 7, wherein the foam-forming composition is formulated to provide the foam having a melting point below 37° C.

10. The foam-forming composition according to claim 7, wherein the buffer is lactic acid.

11. The foam-forming composition according to claim 7, wherein upon dilution 10 times the pH remains in the range of 3 to 5.

12. The foam-forming composition according to claim 7, wherein the foam-forming composition is storage stable.

13. The foam-forming composition according to claim 7, wherein the foam-forming composition is pressurized by the blowing agent.

14. The foam-forming composition according to claim 7, wherein the foam-forming composition is packaged together with instructions for use for the treatment of vaginal, oral, anal, urethral, nasal and ear infections.

15. The foam-forming composition according to claim 14, wherein the instructions for use comprise use for local treatment of sexually transmitted diseases.

16. The foam-forming composition according to claim 15, wherein the foam-forming composition is packaged together with instructions for use for local treatment of sexually transmitted diseases.

17. The foam-forming composition according to claim 7, wherein the foam-forming composition contains at least one stabilizer for hydrogen peroxide.

18. A method of treating an infection or disease in a body cavity comprising:
blowing a foam-forming composition comprising water, a pharmaceutically effective amount of hydrogen peroxide, and solid lipid crystals suspended in the water and having a continuous repeated structure in three dimensions in which the repeated structure is bilayers of water and the solid lipid crystals in one direction, the solid lipid crystals having a melting point in their crystalline state of less than 37° C. and more than 25° C., to form a foam, wherein a blowing agent for forming the foam consists essentially of at least one blowing agent selected from nitrogen, oxygen, or carbon dioxide;
applying the foam to a body cavity; and
allowing the body to heat the foam to a decomposition temperature of the foam to degrade the foam and release the hydrogen peroxide to tissues within the body cavity.

19. The method according to claim 18, wherein the body cavity is a vaginal cavity, urethra cavity, anal cavity, oral cavity, nasal cavity, or ear cavity.

20. A method of treating an infection or disease in a body cavity comprising:
blowing a foam-forming composition comprising water, a pharmaceutically effective amount of hydrogen peroxide, monoglyceride crystals suspended in the water and having a continuous repeated structure in three dimensions in which the repeated structure is bilayers of water and the monoglyceride crystals in one direction, and an acid and/or buffer to form a foam, wherein a blowing agent for forming the foam consists essentially of at least one blowing agent selected from nitrogen, oxygen, or carbon dioxide: applying the foam to a body cavity; and
allowing the body to heat the foam to a decomposition temperature of the foam to degrade the foam and release the hydrogen peroxide to tissues within the body cavity at a pH of 3 to 5, wherein the acid and/or buffer is present in an amount to provide a pH of 3 to 5 within a body cavity.

21. A foam-forming pharmaceutical composition for delivering hydrogen peroxide to a body cavity comprising:
water;
a pharmaceutically effective amount of hydrogen peroxide;
solid lipid crystals suspended in the water and having a continuous repeated structure in three dimensions in which the repeated structure is bilayers of water and the solid lipid crystals in one direction, the solid lipid crystals having a melting point in their crystalline state of less than 37° C. and more than 25° C.; and
a propellant for blowing the composition and forming a foam, the propellant consists essentially of at least one blowing agent selected from nitrogen, oxygen, or carbon dioxide, wherein the solid lipid crystals being present in an amount to support a foam when the composition is blown by the propellant, and the composition is adapted for application to the body cavity when blown so that when the foam is heated by the body cavity the foam degrades at the melting point and releases the hydrogen peroxide to tissues in the body cavity, further comprising: a container; a bag contained in the container, the bag containing the composition; and a valve connected to the container and bag constructed to release the composition from the bag and container.

* * * * *